United States Patent [19]

Ramprasad et al.

[11] Patent Number: 5,728,901
[45] Date of Patent: Mar. 17, 1998

[54] NITRATION PROCESS WHICH EMPLOYS WATER TOLERANT LEWIS ACID CATALYSTS

[75] Inventors: Dorai Ramprasad; Francis Joseph Waller, both of Allentown, Pa.; Anthony Gerard Barrett; David Christopher Braddock, both of London, England

[73] Assignee: Air Products and Chemicals, Inc., Allentown, Pa.

[21] Appl. No.: 720,938

[22] Filed: Oct. 4, 1996

[51] Int. Cl.$^6$ ................................................ C07C 205/00
[52] U.S. Cl. .................... 568/930; 568/927; 568/932; 568/934; 568/937; 568/938; 568/939; 568/940; 568/929
[58] Field of Search ........................ 568/924, 927, 568/928, 930, 931, 932, 933, 934, 937, 938, 939, 940, 929

[56] References Cited

U.S. PATENT DOCUMENTS 4,600,702  7/1986  Schumacher ........................... 502/200

OTHER PUBLICATIONS

R.B. Temple, G.W. Thickett, Australian Journal of Chemistry, 1973, vol. pp. 667–669, Dec. 1973.
V.S. Kalishevich, O.S. Timofeev, K.S. Zakharov, A.I. Gren, Journal of Organic Chemistry of the USSR, 1988, vol. 24, pp. 349–353, Feb. 1988.
A.J. Gordon, R.A. Ford, "The Chemist's Companion", Wiley and Sons, New York, 1972, pp. 145–147.

*Primary Examiner*—Charles T. Jordon
*Assistant Examiner*—John R. Hardee
*Attorney, Agent, or Firm*—Keith D. Gourley

[57] ABSTRACT

A process for preparing a nitrated arene which comprises reacting an arene and nitric acid in the presence of a water tolerant Lewis acid catalyst under process conditions sufficient to form the nitrated arene and recovering the nitrated arene. Suitable Lewis acid catalysts are represented by the formula $M^n(A_1)_x(A_2)_{n-x}$ wherein M is selected from the group consisting of La, Pr, Nd, Sm, Eu, Gd, Dy, Ho, Er, Tm, Yb, Sc, Hf, Lu and Li;

$A_1$ and $A_2$ are independently selected from a perfluoroalkylsulfonate, a fluorosulfonate, a hexafluorophosphate or a nitrate;

n is the common oxidation state of M and x is 1, 2, 3 or 4 with the proviso that x is never greater than n.

The catalysts of the process are isolatable from water and can be recycled for subsequent process cycles.

9 Claims, No Drawings

NITRATION PROCESS WHICH EMPLOYS WATER TOLERANT LEWIS ACID CATALYSTS

TECHNICAL FIELD OF THE INVENTION

This invention relates to a catalytic process for nitrating arenes which are capable of undergoing electrophilic substitution reactions. The nitration process comprises reacting an arene to be converted to its corresponding nitrated arene in the presence of nitric acid and a catalyst comprising specified salts of a Group I metal, a rare earth metal or a transition metal to form the corresponding nitrated amine.

BACKGROUND OF THE INVENTION

Conventional processes for nitrating aromatic compounds comprise reacting an aromatic compound with a catalyst in the presence of nitric acid under reaction conditions sufficient to convert the aromatic compound to its corresponding nitrated aromatic compound. The catalyst serves to facilitate formation of the nitronium ion as well as a water sink. Conventional nitration processes employ a wide variety of Bronsted acids such as sulfuric acid, phosphoric acid, and trifluoromethanesulfonic acid.

Certain Lewis acid catalysts are known in the art as nitration catalysts. For example, o-nitrotoluene can be reacted in the presence of nitric acid and a boron trifluoride catalyst under reaction conditions sufficient to form dinitrotoluene. Another nitration process which utilizes a Lewis acid catalyst employs aluminum chloride which is added to a metal nitrate. Nitration chemistry has been reviewed by G. A. Olah et al., in the book "Nitration: Methods and Mechanisms", VCH Publishers 1989. G. A. Olah et al., have also studied mixed nitric-trifluoroboric acid for the nitration of arenes published in J. Org. Chem. 1995, 60, 7348.

Existing nitration processes which employ catalysts consisting of Bronsted acids, Lewis acids or combinations of Bronsted and Lewis acids are very water sensitive. Those of ordinary skill in the nitration art recognize that Lewis acids can inherently be hydrolyzed by water. Japanese researchers (Synlett, Sept 94, p689) recently reported that rare earth (lanthanide) trifluoromethanesulfonates (triflates) and selected transition metal triflates are suitable water-tolerant Lewis acid catalysts for a variety of organic reactions such as Aldol, Michael, Alkylation and Diels-Alder.

Researchers are searching for a catalytic process for nitrating aromatic compounds which employs Lewis acid catalysts wherein such catalysts are not degraded or rendered inactive in the presence of water formed during the nitration process and wherein water does not have to be separated from the reaction product mixture prior to performing another process cycle.

BRIEF SUMMARY OF THE INVENTION

The present invention relates to a process for preparing a nitrated arene which comprises reacting an arene and nitric acid in the presence of a catalyst under process conditions sufficient to form the nitrated arene and recovering the nitrated arene wherein the catalyst is represented by the formula $M^n(A_1)_x(A_2)_{n-x}$ wherein M is selected from the group consisting of La, Pr, Nd, Sm, Eu, Gd, Dy, Ho, Er, Tm, Yb, Sc, Hf, Lu and Li;

$A_1$ and $A_2$ are independently selected from a perfluoroalkylsulfonate, a fluorosulfonate, a hexafluorophosphate or a nitrate;

n is the common oxidation state of M and x is 1, 2, 3 or 4 with the proviso that x is never greater than n.

Applicants have discovered that while a majority of the Lewis acid catalysts of the present invention provide a product isomer distribution ordinarily observed in conventional electrophilic substitution reactions, the metal nitrate catalysts of the present invention ($A_1$ and $A_2$ are $NO_3$) provide a non-conventional isomer distribution. Such metal nitrate catalysts are represented by the formula $M^n(NO_3)_x$ wherein M is selected from the group consisting of La, Pr, Nd, Sm, Eu, Gd, Dy, Ho, Er, Tm, Yb, Sc, Hf, Lu and Li;

n is the common oxidation state of M and x is equal to n.

Applicants' process utilizes Lewis acid catalysts which are not water sensitive thereby overcoming one of the most significant problems associated with prior art nitration processes which employ Lewis acid catalysts. The catalysts of the present nitration process afford additional advantages over prior art Lewis acid nitration catalysts in that the catalysts are isolatable from water and can be recycled to the nitration process. Moreover, the use of the present water tolerant Lewis acids in the nitration process enables the process to be operated using more dilute nitric acid than was capable in prior art processes.

Arenes capable of undergoing the nitration process are defined as hydrocarbons containing at least one aromatic ring and are represented by Formula I:

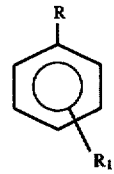

wherein R and $R_1$ are independently selected from a hydrogen atom, a primary, secondary or tertiary alkyl having from 1 to 6 carbon atoms, a halide, $CO_2H$, $OCH_3$, $NHCOCH_3$, $C_6H_5$, OH, $NH_2$ and $NO_2$ with the proviso that when R is a hydrogen atom then $R_1$ is not $NO_2$.

Alternately, the arenes to be nitrated according to the present process include hydrocarbons which possess two or more aromatic rings as presented by Formula II:

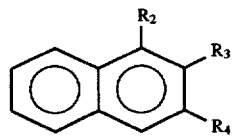

wherein $R_2$, $R_3$ and $R_4$ are independently selected from a hydrogen atom, a primary, secondary or tertiary alkyl having from 1 to 6 carbon atoms, a halide, $CO_2H$, $OCH_3$, $NHCOCH_3$, $C_6H_5$, OH, $NH_2$ and $NO_2$. According to Formula II, each of $R_2$, $R_3$ and $R_4$ may be a hydrogen atom in which case the arene is naphthalene. When $R_2$ is a hydrogen atom and $R_3$ and $R_4$ form a connecting CHCHCHCH bridge then the arene is anthracene. When $R_2$ and $R_3$ form a connecting CHCHCHCH bridge and $R_4$ is a hydrogen atom, then the arene is phenanthrene.

The claimed process can be carried out in a batch reactor or a continuous flow reactor under a broad range of reaction conditions including temperatures ranging from 20° C. to 125° C. and pressures ranging from 1 atmosphere to 50 atmospheres. Preferably, the process is operated at a temperature ranging from 50° C. to 100° C. and pressures ranging from 1 atmosphere to 30 atmospheres. Moreover, the process does not utilize highly corrosive reactants and catalysts which typically require special handling and which may cause damage to the process reactor under certain conditions.

DETAILED DESCRIPTION OF THE INVENTION

The present invention is a process for producing nitrated arenes which utilizes a new class of catalysts which are not sensitive to water and which are readily separable from water. Moreover the catalysts of the present process enable the process to be operated using lower concentrations of nitric acid. The present invention simplifies prior art processes for producing nitrated arenes by eliminating the necessity for tedious washing steps with basic solutions to remove residual acid catalysts from the reaction products.

The process can be conducted at any combination of temperatures and pressures at which the process proceeds to form the desired nitrated arene. Reaction conditions suitable for practicing the present invention will vary depending upon the particular arene to be nitrated according to the process. The rate of formation of the desired nitrated arene shall depend upon the concentration of the nitric acid, catalyst concentration and the reaction temperature. Depending on the initial structure of the arene to be nitrated, the mono-nitro product formed under the process can undergo an additional nitration step to form the corresponding di-nitro arene. However, the reaction temperature and nitric acid concentration required for the second nitration step is more vigorous and reaction temperatures greater than 75° C. are usually required.

Arenes capable of being nitrated according to the present process are defined according to the definition presented in Grant & Hackh's Chemical Dictionary, Fifth Ed., McGraw-Hill, Inc., 1987, namely, a hydrocarbon containing at least one aromatic ring. The word "aromatic" refers to an unsaturated cyclic hydrocarbon in which the electrons are delocalized according to principles well understood in the art. Suitable arenes for practicing the present process are those arenes which are capable of undergoing electrophilic substitution reactions. A representative summary of arenes capable of undergoing electrophilic substitution reactions is presented in Advanced Organic Chemistry, 3rd Ed., March, McGraw-Hill, Inc., 1985. Such arenes include benzene, substituted benzenes, fused-ring compounds where the arene is naphthalene, anthracene or phenanthrene and their derivatives. Arenes which possess a single aromatic ring are represented by the following Formula I.

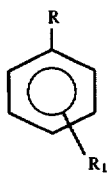

I wherein R and $R_1$ are independently selected from a hydrogen atom, a primary, secondary or tertiary alkyl having from 1 to 6 carbon atoms, a halide, (i.e. fluoride, chloride, iodide or bromide), $CO_2H$, $OCH_3$, $NHCOCH_3$, $C_6H_5$, OH, $NH_2$ and $NO_2$ with the proviso that when R is a hydrogen atom then $R_1$ cannot be $NO_2$.

Preferred arenes represented by Formula I which are capable of being nitrated according to the present process include benzene, toluene, ethylbenzene, t-butylbenzene, chlorobenzene, anisole, acetanilide, biphenyl, phenol, o-nitrotoluene, p-nitrotoluene, m-xylene, p-xylene, m-cresol, cumene, isophthalic acid and o-toluic acid Most preferred arenes to be nitrated according to the present process include benzene, toluene and a mixture of o-, m- and p-nitrotoluenes wherein the catalyst is either scandium (III) triflate or ytterbium (III) triflate.

Arenes to be nitrated according to the present process include hydrocarbons which possess two or more aromatic rings as presented by Formula II

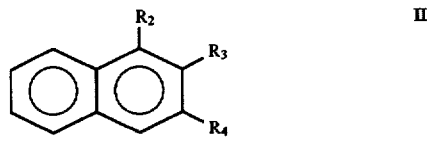

II wherein $R_2$, $R_3$ and $R_4$ are independently selected from a hydrogen atom, a primary, secondary or tertiary alkyl having from 1 to 6 carbon atoms, a halide (i.e. fluoride, chloride, iodide or bromide), $CO_2H$, $OCH_3$, $NHCOCH_3$, $C_6H_5$, OH, $NH_2$ and $NO_2$ According to Formula II, each of $R_2$, $R_3$ and $R_4$ may be a hydrogen atom in which case the arene is naphthalene. When $R_2$ is a hydrogen atom and $R_3$ and $R_4$ form a connecting CHCHCHCH bridge then the arene is anthracene. When $R_2$ and $R_3$ form a connecting CHCHCHCH bridge and $R_4$ is a hydrogen atom, then the arene is phenanthrene.

The arenes represented by Formulae I and II can be subjected to the present process to form the corresponding mono nitrated arene wherein one nitro group is introduced into the arene with the proviso that nitrobenzene does not form dinitrobenzene under process conditions studied by the Applicants. Alternately, the mono-nitrated arenes can be subjected to the present process to form the corresponding di-nitrated arene wherein two nitro groups are introduced in arene. One of ordinary skill in art can readily identify substituted arenes which are capable of being converted to valuable commercial products using the claimed process.

Nitrated arenes of particular interest made suitable for preparation by the claimed process include nitrobenzene, o-nitrotoluene, p-nitrotoluene, 2,4-dinitrotoluene, 2,6-dinitrotoluene, 2 and 4-nitrochlorobenzene, 1-nitronaphthalene, 1,5- and 1,8-dinitronaphthalene, o-and p-nitrophenol, and 2,4-dinitrophenol.

The water tolerant Lewis acid catalysts of the present invention are represented by the generic formula $M^n(A_1)_x (A_2)_{n-x}$ wherein M is selected from the group consisting of La, Pr, Nd, Sm, Eu, Gd, Dy, Ho, Er, Tm, Yb, Sc, Hf, Lu and Li;

$A_1$ and $A_2$ are independently selected from a perfluoroalkylsulfonate, a fluorosulfonate, a hexafluorophosphate or a nitrate;

n is the common oxidation state of M and x is 1, 2, 3 or 4 with the proviso that x is never greater than n.

For purposes of interpreting the catalyst formula, the common oxidation state (n) of Li is 1; the common oxidation state of Hf is 4; and the common oxidation state of La, Pr, Nd, Sm, Eu, Gd, Dy, Ho, Er, Tm, Yb, Sc and Lu is 3. If M is Hf, then n is 4, and x can be 1, 2, 3 or 4. If x is 4, then the catalyst is represented by $Hf^{4+}(A_1)_4$ and the catalyst does not possess anion $A_2$ based upon the formula n-x because 4−4=0. If x is 3, then the catalyst is represented by $Hf^{3+}(A_1)_3(A_2)$. Each $A_1$ and $A_2$ can be independently selected from a perfluoroalkylsulfonate, a fluorosulfonate, a hexafluorophosphate or a nitrate.

The Lewis acid catalysts of the present invention can be formed from anions wherein $A_1$ is the same as $A_2$. For example, suitable catalysts include those formed from perfluoroalkylsulfonates where the alkyl moiety is methane, butane or nonane. More commonly the perfluoroalkylsulfonates are called trifluoromethanesulfonates (triflates), nonafluorobutanesulfonates or heptadecafluorononanesulfonates. The active catalyst can also be formed from two different anions where $A_1$ is different from $A_2$. Examples of catalysts formed from different anions include the catalysts wherein $A_1$ is a hexafluorophosphate and $A_2$ is either the perfluoroalkylsulfonate or the fluorosulfonate.

Applicants have discovered that while a majority of the Lewis acid catalysts of the present invention provide a product isomer distribution ordinarily observed in conventional electrophilic substitution reactions, the metal nitrate catalysts of the present invention ($A_1$ and $A_2$ are $NO_3$) provide a non-conventional isomer distribution. Such metal nitrate catalysts are represented by the formula $M^n(NO_3)_x$ wherein M is selected from the group consisting of La, Pr, Nd, Sin, Eu, Gd, Dy, Ho, Er, Tm, Yb, Sc, Hf, Lu and Li;
n is the common oxidation state of M and
X is equal to n.

The ratio of the ortho and para substituted arenes can be altered by varying the metal (M) identified in the catalyst formula. For example, when the arene is toluene and when M is lithium, then the nitration process favors formation of the ortho isomer whereas when M is scandium, then the nitration process favors formation of the para isomer. This result is commercially valuable and provides a useful route to favoring formation of a desired isomer.

Nitric acid to be used in the claimed process can vary widely in concentration and is preferably in the range of 90 wt % $HNO_3$ to 20 wt % $HNO_3$. Most preferred is nitric acid having a concentration is 68–70 wt % for mono-nitration.

A solvent may be used in the present process although the arene alone may serve as the process medium. Suitable solvents for practicing the present process include any solvent or mixture of solvents wherein the solvent is inert with respect to the reactants under the enumerated process conditions. The term, inert, means that the solvent will not react with the arene or nitric acid under the chosen process conditions. Suitable solvents include chlorinated solvents such as dichloromethane or 1,2-dichloroethane.

The final step in the nitration process consists of separating the nitrated arene from the process medium. This step can be accomplished by conventional methods including distillation and fractional recrystallization. Preferably, the nitrated arene is separated from the reaction medium by any known distillation technique.

The following examples are provided to illustrate the process of the present invention and should not be construed as limiting the scope thereof.

EXPERIMENTAL SECTION

EXAMPLE 1

Nitration of Toluene Catalyzed by Lanthanide Triflates

Runs 1 through 5 presented in Table 1 illustrate the results obtained by nitrating toluene with various water tolerant Lewis acid catalysts according to the claimed process. According to each Run, the specified catalyst (3.3 mmol), 70% $HNO_3$ (16.7 mmol) and toluene(30 g, 0.325 mol) were weighed separately. The catalyst was suspended in toluene and the nitric acid was added with stirring. The flask was fitted with a condenser and the mixture was heated under nitrogen for 5 hours. The resulting reaction mixture was neutralized with $NaHCO_3$, and analyzed by gas chromatography.

TABLE 1

NITRATION OF TOLUENE CATALYZED BY LANTHANIDE TRIFLATES

| Run | Catalyst | Temp (°C.) | Yield* (%) | Distribution (%) | | |
|---|---|---|---|---|---|---|
| | | | | o-nitro | m-nitro | p-nitro |
| 1 | Sc(OTf)$_3$ | 60 | 79.0 | 54.0 | 3.3 | 42.7 |
| 2 | Sc(OTf)$_3$ | 25 | 63.0 | 54.8 | 3.0 | 42.2 |
| 3 | Yb(OTf)$_3$ | 60 | 47.6 | 55.3 | 3.7 | 41.0 |
| 4 | La(OTf)$_3$ | 60 | 37.4 | 55.1 | 6.8 | 38.1 |
| 5 | Sc(NO$_3$)$_3$.4H$_2$O | 60 | 25.4 | 35.0 | 3.7 | 61.3 |

*Yield based on nitric acid added

Runs 1 through 4 demonstrate the catalytic activity of the specified metal triflates whereas Run 5 illustrates the catalytic activity of scandium nitrate. Runs 1 and 2 demonstrate that Sc(OTf)$_3$ is an efficient catalyst providing nitro-toluene yields of 79% and 63%, respectively. Runs 3 and 4 demonstrate that Yb(OTf)$_3$ and La(OTf)$_3$ also provide respectable yields of nitro-toluene. Run 5 illustrates the catalytic activity of Sc(NO$_3$)$_3$ wherein o-nitrotoluene and p-nitrotoluene are formed in a 35.0:61.3 ratio. These Runs illustrate that the process operator can control product distribution to an extent by choosing a catalyst which favors a given isomer distribution. No formation of dinitrotoluenes was observed at a process operating temperature of 60° C.

EXAMPLE 2

Nitration of m-Xylene Catalyzed by Lanthanide Triflates

Runs 6 through 10 presented in Table 2 illustrate the results obtained by nitrating m-xylene using catalysts comprising selected triflates. In each Run, 69% nitric acid (3.0 mmol) was added to a stirred suspension of the specified triflate (0.30 mmol) in dichloromethane (15 ml). The suspension solubilised to give a two phase system in which the aqueous phase was the more dense. m-xylene (3.0 mmol) was added and the stirred mixture was heated at reflux for 18 h. The solution was allowed to cool and diluted with water. The yellow organic phase was dried over $MgSO_4$ and evaporated to give nitroxylenes. The conversion and product distribution is shown in Table 2.

TABLE 2

NITRATION OF M-XYLENE CATALYZED BY LANTHANIDE TRIFLATES*

| Run | (OTf)$_3$[b] | Conversion (%)[c] | Distribution (%)[c] | |
|---|---|---|---|---|
| | | | 4-NO$_2$ | 2-NO$_2$ |
| 6 | La | 22 | 86 | 14 |
| 7 | Eu | 36 | 86 | 14 |
| 8 | Pr | 65 | 88 | 12 |
| 9 | Sc | 85 | 85 | 15 |
| 10 | Yb | 88 | 85 | 15 |

[a]All reactions performed with 10 mol % lanthanide (III) triflate, 1 equivalent each of m-xylene and 69% nitric acid in refluxing dichloromethane (15 ml) for 18 h.
[b]Commercially available hydrated forms.
[c]GC analysis.

Runs 6 through 10 demonstrate the catalytic activity of triflates formed from a metal selected from the group of lanthanum, europium, praseodymium, scandium and ytterbium. As expected, each Run provides a preference toward the p-nitroarene versus the o-nitroarene. Runs 9 and 10 demonstrate that Sc(OTf)$_3$ and Yb(OTf)$_3$ are efficient catalysts providing conversions of 85% and 85%, respectively.

Experiment 3

Nitration of Arenes with Ytterbium (III) Triflate

Table 3 presents Runs 11 through 15 which illustrate the nitration of the enumerated benzene compounds wherein R represents a substituent on the benzene ring and Runs 16 through 19 which illustrate the nitration of the specified arenes. All Runs were carried out on 3 mmol scale with 10 mol % ytterbium (III) triflate and 1 equivalent of 69% nitric acid in refluxing 1,2-dichloroethane (5 ml) for 12 hours.

TABLE 3

NITRATION OF ARENES WITH YTTERBIUM (III) TRIFLATE

| Run | R | Conversion (%)[a,b] | Distribution (%)[b] | | |
|---|---|---|---|---|---|
| | | | ortho | meta | para |
| 11 | H | >75 (75) | — | — | — |
| 12 | Me | >95 (95) | 52 | 7 | 41 |
| 13 | Ph | 89 | 38 | trace | 62 |
| 14 | Br | 92 | 44 | trace | 56 |
| 15 | NO$_2$ | 0 | — | — | — |
| 16 | p-xylene | >95 | — | — | — |
| 17 | p-dibromobenzene | 8 | — | — | — |
| 18 | m-xylene | | 4-NO$_2$:85 | | 2-NO$_2$:15 |
| 19 | naphthalene | >95 | 1-NO$_2$:91 | | 2-NO$_2$:9 |

[a]Isolated yields in parenthesis.
[b]GC and/or $^1$H NMR analysis.

The results demonstrate that each of the Runs yield the corresponding nitrated arene with the exception of Run 15 wherein nitrobenzene was not converted to dinitrobenzene under the reaction temperature utilized.

EXAMPLE 4

Nitration of Toluene With Catalyst Recycle

An experiment was performed in order to demonstrate that the catalyst of the claimed process can be recycled. Approximately 3.3 mmol of scandium triflate, 1.5 g (16.7 mmol) of 70% nitric acid and 30 g(0.326 mol) of toluene were heated to 60° C. for approximately 5 hours. The products were analyzed by gas chromatography and an o/m/p ratio of 53.6/3.2/43.1 with an overall yield of 72.4% was obtained. The organics were removed by rotary evaporation and the recovered catalyst was washed thoroughly with pentane to remove any organics. The nitration reaction was now repeated with a fresh charge of reactants to give an overall yield of 57.5% nitro products with an o/m/p ratio of 49.4/3.4/47.1.

Experiment 5

Nitration of m-Xylene With Catalyst Recycle

Runs 20 through 23 presented in Table 4 provide the results obtained by nitrating m-xylene in the presence of varying amounts of recycled yyterbium (III) triflate catalyst. According to each Run, 69% Nitric acid (3.0 mmol) was added to a stirred suspension of ytterbium (III) triflate (186 mg, 0.30 mmol) in 1,2-dichloroethane (5 ml). The suspension solubilised to give a two phase system in which the aqueous phase was the more dense. m-xylene (3.0 mmol) was added and the stirred mixture was heated at reflux for 5 hours. The solution was allowed to cool and diluted with water. The yellow organic phase was dried over MgSO$_4$ and evaporated to give nitro xylenes.

TABLE 4

RECYCLED YTTERBIUM (III) TRIFLATE[a]

| Run | Conversion (%)[b] | Mass of catalyst (mg)[c] |
|---|---|---|
| 20 | 89 | 190 (>100) |
| 21 | 81 | 152 (82) |
| 22 | 90 | 127 (68) |
| 23 | 88 | 115 (62) |

[a]All runs performed with 3 mmol m-xylene, 10 mol % ytterbium triflate (run 1) and 1 equivalent of nitric acid in refluxing 1,2-dichloroethane (5 ml) for 5 h.
[b]GC analysis. The isomeric ratio of 4 and 2-nitroxylene was unchanged throughout (85:15 respectively).
[c]Mass of ytterbium (III) triflate recovered from each run. The figures in parenthesis indicate the percentage recovery.

Runs 20 through 23 demonstrate that the conversion of m-xylene to the corresponding nitrated products remains constant even though minor amounts of the catalysts were not recovered during each process cycle.

EXAMPLE 6

Nitration of o-Nitrotoluene to Dinitrotoluene

Run 24 presented in Table 5 illustrates results obtained by nitrating o-nitrotoluene using a catalyst comprising scandium (III) triflate. Run 25 is a comparative example wherein the catalyst comprises triflic acid. According to Run 24, approximately 3.3 mmol of scandium triflate, 1.5 g(16.7 mmol) of 70% nitric acid and 45 g(0.326 mol) of o-nitrotoluene was heated to 80° C. for 5 h. The reaction mixture was neutralized by NaHCO$_3$ and analyzed by gas chromatography.

TABLE 5

NITRATION OF O-NITROTOLUENE BY SCANDIUM (III) TRIFLATE

| Run | Catalyst (mmol) | Yield (%) | Distribution (%) | |
|---|---|---|---|---|
| | | | 2,4-DNT | 2,6-DNT |
| 24 | Sc(OTf)$_3$ (3.3) | 8.8 | 66 | 34 |
| 25* | HOTf (9.7) | 5.2 | 66 | 34 |

*comparative example

Run 24 demonstrates that Sc(OTf)$_3$ is a better catalyst for dinitration than the equivalent amount of triflic acid as presented in Run 25.

EXAMPLE 7

Nitration of Toluene with Lithium Triflate

Runs 26 through 29 presented in Table 6 illustrate the nitration of toluene using lithium triflate as the water tolerant Lewis Acid. The catalysts in Table 6 were suspended in 70% nitric acid(8.3 mmol), and toluene(15 g, 0.162 mol) was added. The mixture was stirred at room temperature(20° C.) for 5 hours, after which the reaction mixture was neutralized with NaHCO$_3$ and analyzed by gas chromatography. The results of the experiment are shown below.

TABLE 6

NITRATION WITH LITHIUM TRIFLATE

| Run | catalyst | mmoles | yield %* | Distribution (%) | | |
|---|---|---|---|---|---|---|
| | | | | o-nitro | m-nitro | p-nitro |
| 26 | LiOTf | 3.1 | 23.5 | 55.9 | 3.4 | 40.7 |
| 27 | LiNO$_3$ | 7.2 | 2.5 | 66.1 | 3.8 | 30.1 |
| 28 | Mg(OTf)$_2$ | 3.1 | 3.6 | 53.3 | 5.1 | 41.6 |
| 29 | no catalyst | — | 2.8 | 59.3 | 4.6 | 36.1 |

*Yield based on added nitric acid

The results demonstrated that lithium triflate is an effective Lewis acid catalyst for nitrating toluene. Runs 26 and 27 illustrate that product isomer distribution can be varied by selecting the anion associated with the metal (M) of the water tolerant Lewis acid catalyst.

EXAMPLE 8

Mono-Nitration of Toluene Under Varying HNO$_3$ Concentration

Runs 30, 31 and 32 demonstrate the results obtained by nitrating toluene while varying the concentration of nitric acid. According to each Run, nitric acid (0.75 g, 70% by weight) was dissolved in scandium triflate (0.8 g) with stirring. The reaction flask was placed in an oil bath at 60° C., and then toluene (15 g) was added. Samples were withdrawn as a function of time and analyzed for ortho, meta, and para nitrotoluenes. At the end of 5–6 hours the reaction was considerably slowed down, and based on the amount of product formed the concentration of the nitric acid at the end of the reaction was calculated. The reaction was repeated using nitric acid (1.05 g, 50% by weight) and finally with 1.75 g of nitric acid (30% by weight), and the final concentrations of nitric acid were calculated. The results are shown in the Table 7.

TABLE 7

MONO-NITRATION OF TOLUENE AT DIFFERENT HNO$_3$ CONCENTRATIONS

| Run | Start HNO3 concentration | Final HNO3 concentration | Yield % a,b |
|---|---|---|---|
| 30 | 70% | 21.0% | 81.9 |
| 31 | 50% | 26.6% | 57.8 |
| 32 | 30% | 22.8% | 28.5 | a Yield based on added nitric acid
b Typical o,m,p isomer distribution is 57.2, 3.9, 38.9%

Runs 30 through 32 show that the nitration rate slows down as the acid concentration approaches 20% by weight.

EXAMPLE 9

Nitration of o-Nitrotoluene

The effect of water on the nitration of o-nitrotoluene is described in Runs 33 and 34 presented in Table 8. In each Run, scandium triflate (0.8 g) was dissolved in 70% nitric acid (0.8 g), and to this was added 22.5 g of o-nitrotoluene. After heating to 80° C. for 5 hours, the products were analyzed by gas chromatography. The experiment was repeated with a 50% nitric acid (1.12 g) and the results are shown below.

TABLE 8

NITRATION OF o-NITROTOLUENE

| Run | nitric acid composition (wt %) | product (mmol) 2,6 DNT + 2,4 DNT | Ratio 2,6:2,4 |
|---|---|---|---|
| 33 | 70% | 2.46 | 33:67 |
| 34 | 50% | 0.18 | 35:65 |

Run 33 shows that a 29.4% yield is obtained when 70% nitric acid is utilized in the process and represents the best results obtained for dinitration. The previous best yield was 6%, however in that experiment the amount of o-nitrotoluene used was much greater. Run 34 shows that the nitration rates substantially decreases when the nitric acid concentration used in the process is reduced from 70% to 50% nitric acid.

From the results it can be concluded that rate of dinitration is more sensitive to water content than mononitration.

EXAMPLE 10

Nitration of Toluene with Lithium Based Lewis Acid Catalysts

Runs 26, 27 and 29 (previously discussed) and Runs 35 and 36 presented in Table 9 illustrate the results obtained in the nitration of toluene when the anion of the Lewis acid catalyst is varied. According to the catalyst based Runs, catalyst was suspended in 70% nitric acid (8.3 mmol), and toluene (15 g, 0.162 mol) was added. The mixture was stirred at room temperature (20° C.) for 5 hours, after which the products were neutralized with NaHCO$_3$ and analyzed by gas chromatograph. The results follow:

TABLE 9

NITRATION OF TOLUENE WITH LITHIUM BASED LEWIS ACID CATALYSTS

| Run | catalyst | mmoles | yield %* | o-nitro | m-nitro | p-nitro |
|---|---|---|---|---|---|---|
| 26 | LiOTf | 3.1 | 23.5 | 55.9 | 3.4 | 40.7 |
| 27 | LiNO$_3$ | 7.2 | 2.5 | 66.1 | 3.8 | 30.1 |
| 29 | no catalyst | — | 2.8 | 59.3 | 4.6 | 36.1 |
| 35 | LiPF$_6$ | 3.1 | 30.5 | 58.8 | 3.9 | 37.3 |
| 36 | LiBF$_4$ | 2.8 | 4.5 | 58.4 | 5.3 | 36.3 |

*Yield based on added nitric acid.

The Runs presented in Table 9 show that the catalytic activity decreases in the sequence LiPF$_6$>LiOTf>LiBF$_4$>LiNO$_3$.

The results according to the present invention demonstrate that the Lewis acid catalysts of the present invention overcome problems associated with prior art nitration processes in that such catalysts are not sensitive to water and are readily separable from water. Moreover the catalysts of the present process enable the process to be operated using lower concentrations of nitric acid. The present invention simplifies prior art processes for producing nitrated arenes by eliminating the necessity for tedious washing steps with basic solutions to remove residual acid catalysts from the reaction products.

Having thus described the present invention, what is now deemed appropriate for Letters Patent is set forth in the following claims.

We claim:

1. A process for preparing a nitrated arene which comprises reacting an arene represented by the formulae

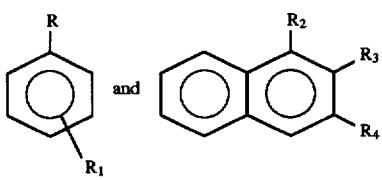

wherein R and $R_1$ are independently selected from a hydrogen atom, a primary, secondary or tertiary alkyl having from 1 to 4 carbon atoms, a halide, $CO_2H$, $OCH_3$, $NHCOCH_3$, $C_6H_5$, OH, $NH_2$ and $NO_2$ with the proviso that when R is a hydrogen atom then $R_1$ cannot be $NO_2$; and $R_2 R_3$ and $R_4$ are independently selected from a hydrogen atom, a primary, secondary or tertiary alkyl having from 1 to 4 carbon atoms, a halide, $CO_2H$, $OCH_3$, $NHCOCH_3$, $C_6H_5$, OH, $NH_2$ and $NO_2$ and wherein each of $R_2$, $R_3$ and $R_4$ is a hydrogen atom; $R_2$ is a hydrogen atom and $R_3$ and $R_4$ form a connecting CHCHCHCH bridge; and $R_2$ and $R_3$ form a connecting CHCHCHCH bridge and $R_4$ is a hydrogen atom; and nitric acid in the presence of a catalyst under process conditions sufficient to form the nitrated arene and recovering the nitrated arene wherein the catalyst is represented by the formula $M^n(A_1)_x(A_2)_{n-x}$ wherein M is selected from the group consisting of La, Pr, Nd, Sm, Eu, Gd, Dy, Ho, Er, Tm, Yb, Sc, Hf, Lu and Li;

$A_1$ and $A_2$ are independently selected from a perfluoroalkylsulfonate, a fluorosulfonate, a hexafluorophosphate or a nitrate;

n is the common oxidation state of M and x is 1, 2, 3 or 4 with the proviso that x is never greater than n with a proviso that $(A_1)_x(A_2)_{n-x}$ is not trinitrate under process conditions sufficient to form the nitrated arene and recovering the nitrated arene.

2. The process according to claim 1 wherein the process conditions comprise a temperature ranging from 25° to 125° C. and a pressure ranging from 1 atmosphere to about 50 atmospheres.

3. The process according to claim 2 wherein the arene is selected from the group consisting of benzene, toluene, ethylbenzene, t-butylbenzene, chlorobenzene, anisole, acetanilide, phenol, o-nitrotoluene, p-nitrotoluene, m-xylene, p-xylene, m-cresol, cumene, and o-toluic acid.

4. The process according to claim 2 wherein the arene in selected from the group consisting of naphthalene, anthracene, phenanthrene and 1-nitronaphthalene.

5. The process according to claim 2 wherein the reaction is carried out in a batch reactor or a continuous flow reactor.

6. The process according to claim 2 wherein the arene is benzene and the catalyst is selected from the group consisting of scandium (III) triflate and ytterbium (III) triflate.

7. The process according to claim 2 wherein the arene is toluene and the catalyst is selected from the group consisting of scandium (III) triflate and ytterbium (III) triflate.

8. The process according to claim 2 wherein the arene is a mixture of nitrotoluenes and the catalyst is selected from the group consisting of scandium (III) triflate and ytterbium (III) triflate.

9. The process according to claim 2 wherein the catalyst is represented by the formula $M^n(NO_3)_x$ wherein M is selected from the group consisting of La, Pr, Nd, Sm, Eu, Gd, Dy, Ho, Er, Tm, Yb, Sc, Hf, Lu and Li;

n is the common oxidation state of M and x is equal to n.

* * * * *